United States Patent
Katayama et al.

(10) Patent No.: US 10,888,691 B2
(45) Date of Patent: Jan. 12, 2021

(54) STENT DELIVERY METHOD

(71) Applicant: OLYMPUS CORPORATION, Tokyo (JP)

(72) Inventors: Tomofumi Katayama, Tokyo (JP); Rei Matsunaga, Tokyo (JP); Tomohiko Mamiya, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 351 days.

(21) Appl. No.: 15/960,673

(22) Filed: Apr. 24, 2018

(65) Prior Publication Data

US 2019/0321605 A1  Oct. 24, 2019

(51) Int. Cl.
*A61M 27/00* (2006.01)

(52) U.S. Cl.
CPC ... *A61M 27/002* (2013.01); *A61M 2210/1053* (2013.01)

(58) Field of Classification Search
CPC ....... A61B 2017/1139; A61F 2002/041; A61F 2250/0039; A61F 2250/0071; A61F 2/00; A61F 2/90; A61F 2/966; A61F 2/97; A61M 2210/10; A61M 2210/1053; A61M 27/002

See application file for complete search history.

(56) References Cited

U.S. PATENT DOCUMENTS

| | | | |
|---|---|---|---|
| 5,662,703 A | 9/1997 | Yurek et al. | |
| 6,620,122 B2 | 9/2003 | Stinson et al. | |
| 2006/0200221 A1 | 9/2006 | Malewicz | |
| 2009/0281379 A1 | 11/2009 | Binmoeller et al. | |
| 2009/0281557 A1 | 11/2009 | Sander et al. | |
| 2010/0094398 A1 | 4/2010 | Malewicz | |
| 2010/0268029 A1 | 10/2010 | Phan et al. | |
| 2010/0268175 A1 | 10/2010 | Lunsford et al. | |
| 2011/0112622 A1 | 5/2011 | Phan et al. | |
| 2011/0137394 A1 | 6/2011 | Lunsford et al. | |
| 2012/0109277 A1 | 5/2012 | Lepulu et al. | |
| 2012/0130417 A1 | 5/2012 | Lepulu et al. | |
| 2012/0136426 A1 | 5/2012 | Phan et al. | |
| 2013/0253546 A1 | 9/2013 | Sander et al. | |
| 2013/0310833 A1 | 11/2013 | Brown et al. | |
| 2014/0236064 A1 | 8/2014 | Binmoeller et al. | |
| 2016/0242846 A1 | 8/2016 | Brown et al. | |
| 2016/0249902 A1 | 9/2016 | Lunsford et al. | |
| 2017/0035426 A1 | 2/2017 | Phan et al. | |

(Continued)

FOREIGN PATENT DOCUMENTS

| | | |
|---|---|---|
| JP | H10-507675 A | 7/1998 |
| JP | 2008-541786 A | 11/2008 |
| JP | 2013-022272 A | 2/2013 |

(Continued)

*Primary Examiner* — Kai H Weng
(74) *Attorney, Agent, or Firm* — Scully, Scott, Murphy & Presser, P.C.

(57) ABSTRACT

A stent delivery method includes: forming through-holes in an alimentary canal wall and a cyst wall so as to communicate with each other; passing a stent through the through-holes and placing a first expandable part in the alimentary canal and a second expandable part in the cyst; allowing the first expandable part to expand to an expanded state in the alimentary canal; and, after the expansion of the first expandable part, allowing the second expandable part to expand in the cyst while the alimentary canal wall is pressed by the first expandable part in the expanded state.

12 Claims, 15 Drawing Sheets

(56) References Cited

U.S. PATENT DOCUMENTS

2017/0035427 A1 2/2017 Sander et al.
2017/0035428 A1 2/2017 Binmoeller et al.

FOREIGN PATENT DOCUMENTS

| JP | 5535313 B | 7/2014 |
|---|---|---|
| WO | 96/32078 A1 | 10/1996 |
| WO | 2006/096229 A | 9/2006 |
| WO | 2010/138277 A1 | 12/2010 |

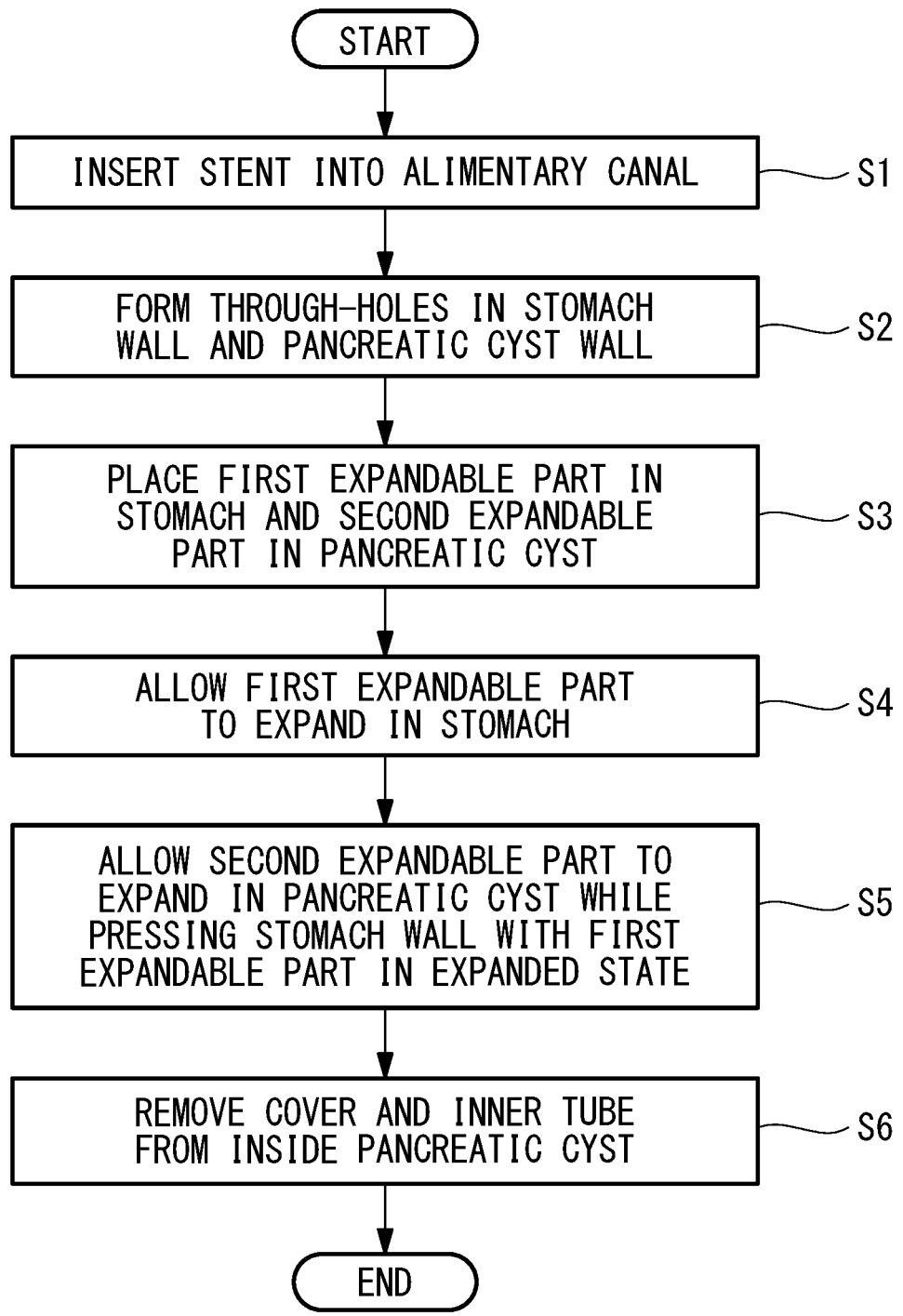

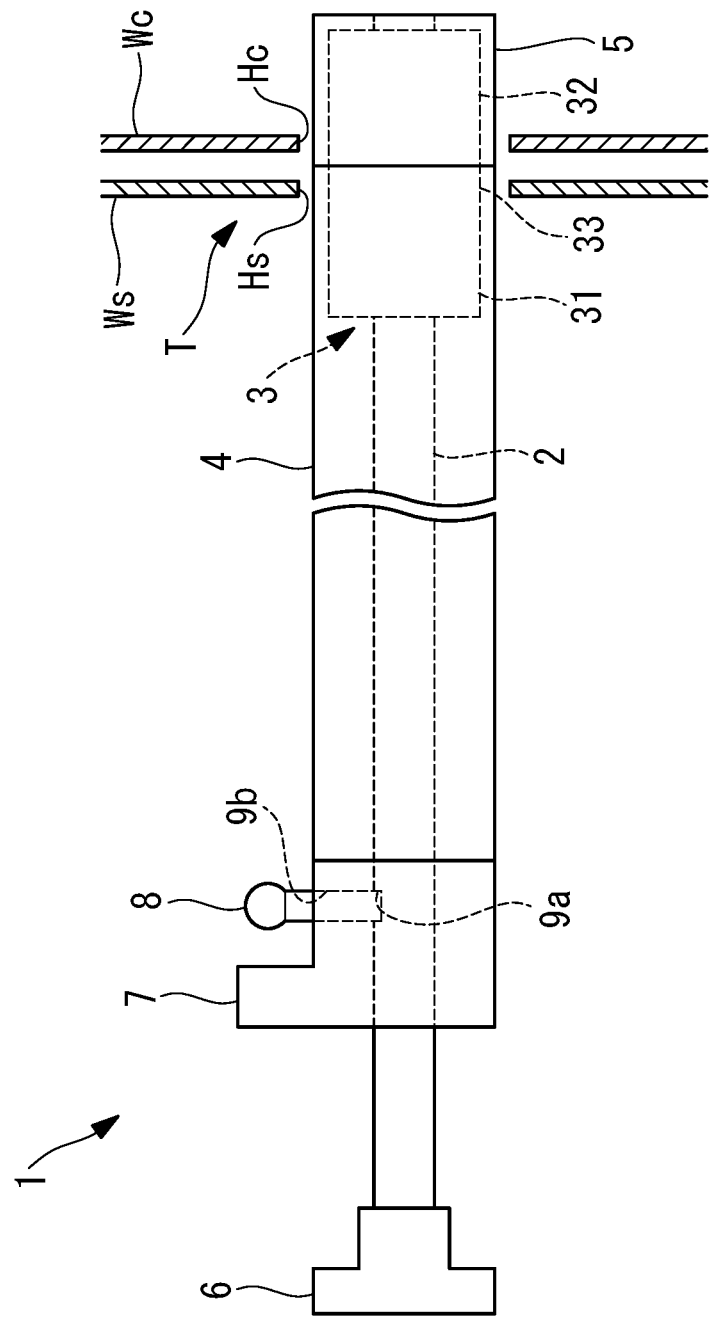

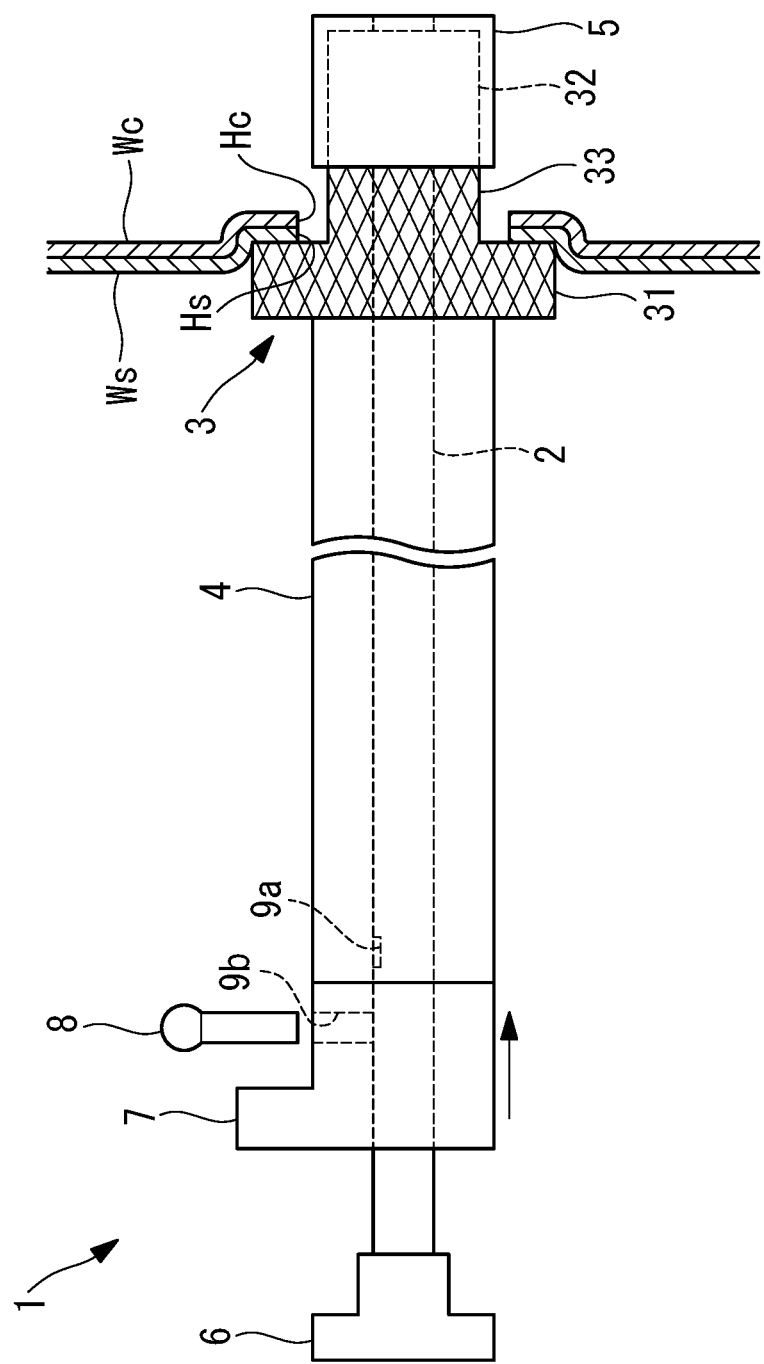

STENT DELIVERY METHOD

TECHNICAL FIELD

The present invention relates to a stent delivery method.

BACKGROUND ART

In a conventional pancreatic cyst drainage for discharging liquid from a pancreatic cyst, a stent having two expandable flanges at both ends thereof is used to communicate between the inside of the stomach and the inside of the pancreatic cyst (for example, see Patent Literature 1). Pancreatic cysts are bag-like tissues that are formed behind the stomach and that store body fluid, such as pancreatic fluid. The stent is placed through the stomach wall and the pancreatic cyst wall, which adjoin each other, by using a delivery device, in accordance with the process including steps 1 to 4 below.

Step 1: A stent is inserted into the pancreatic cyst from the stomach side so as to penetrate through the stomach wall and the pancreatic cyst wall, which adjoin each other.

Step 2: A distal-side flange is expanded in the pancreatic cyst.

Step 3: The distal-side flange is engaged with the pancreatic cyst wall by pulling the delivery device, and the pancreatic cyst wall is brought into tight contact with the stomach wall.

Step 4: A proximal-side flange is expanded in the stomach.

The process including steps 1 to 4 is performed while the delivery device and the stent are observed with an optical endoscope in the stomach. In other words, in step 3, an operator pulls the delivery device in a state in which he/she cannot view the distal-side flange in the pancreatic cyst.

CITATION LIST

Patent Literature

{PTL 1} Japanese Patent No. 5535313

SUMMARY OF INVENTION

An aspect of the present invention is a stent delivery method using a tubular stent having a first expandable part and a second expandable part, the first and second expandable parts being provided at positions away from each other in a direction parallel to a central axis of the stent, the first and second expandable parts being expandable from a non-expanded state to an expanded state, in which the outside diameters of the first and second expandable parts are larger than those in the non-expanded state. The method includes: forming through-holes in an alimentary canal wall and a cyst wall so as to communicate with each other, the cyst being formed outside the alimentary canal, and the cyst wall adjoining the alimentary canal wall; inserting the stent through the through-holes and placing the first expandable part in the alimentary canal and the second expandable part in the cyst; allowing the first expandable part to expand to the expanded state in the alimentary canal; and, after the expansion of the first expandable part, allowing the second expandable part to expand in the cyst while pressing the wall of the alimentary canal with the first expandable part in the expanded state.

BRIEF DESCRIPTION OF DRAWINGS

FIG. 3 is a flowchart for explaining the stent delivery method according to the embodiment of the present invention.

FIG. 4B is a diagram for explaining the stent delivery method according to the embodiment of the present invention.

FIG. 4D is a diagram for explaining the stent delivery method according to the embodiment of the present invention.

DESCRIPTION OF EMBODIMENTS

A stent delivery method according to an embodiment of the present invention will be described below with reference to the drawings.

Figure 1:
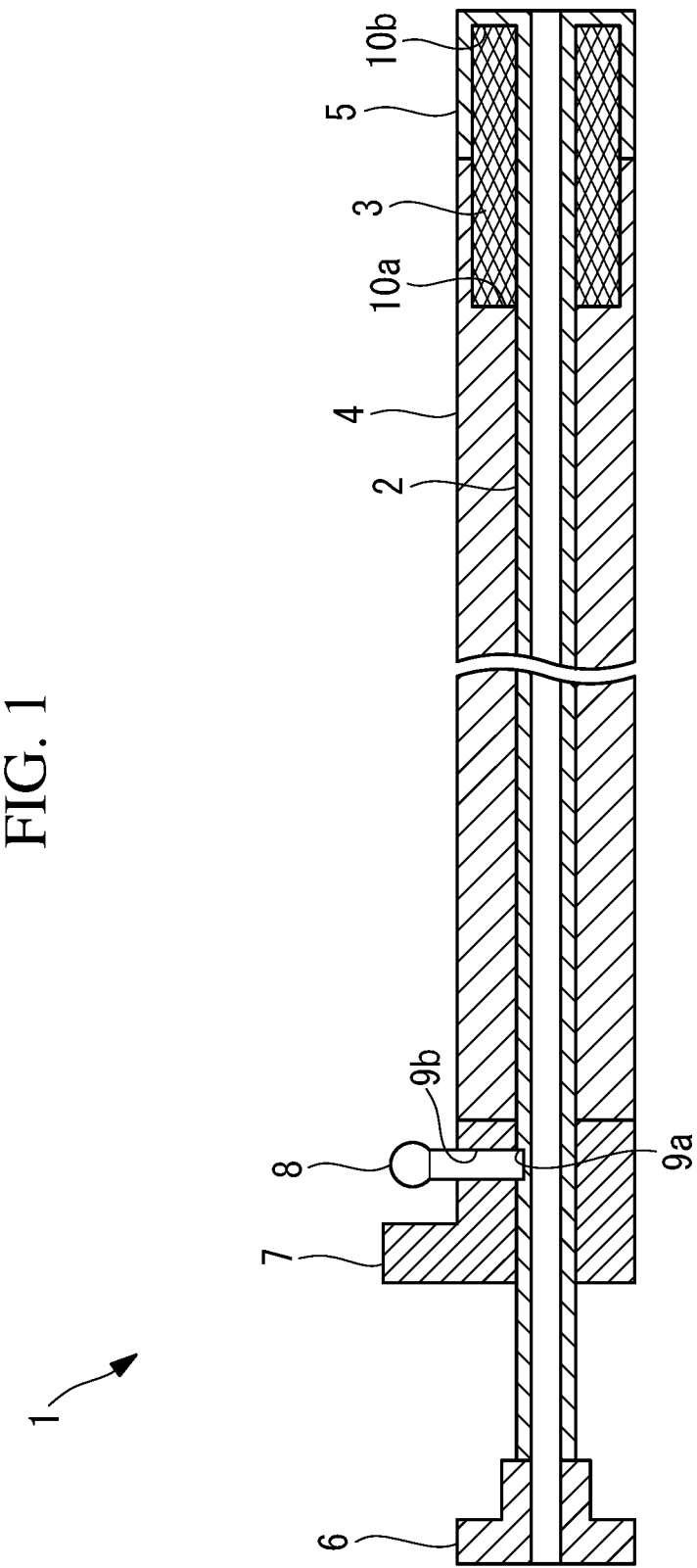
FIG. 1 is a vertical sectional view showing the overall configuration of a stent delivery system used in a stent delivery method according to an embodiment of the present invention.

FIG. 1 shows a stent delivery system 1 used in a stent delivery method according to this embodiment. The stent delivery system 1 includes: an inner tube 2; a tubular stent 3 attached to the distal end portion of the inner tube 2; and an outer sheath 4 and a cover 5, which are disposed outside the inner tube 2 and surround the stent 3.

The inner tube 2 is an elongated circular-tube-like member having flexibility. A handle 6, via which an operator operates the inner tube 2, is joined to the base end of the inner tube 2.

Figure 2A:
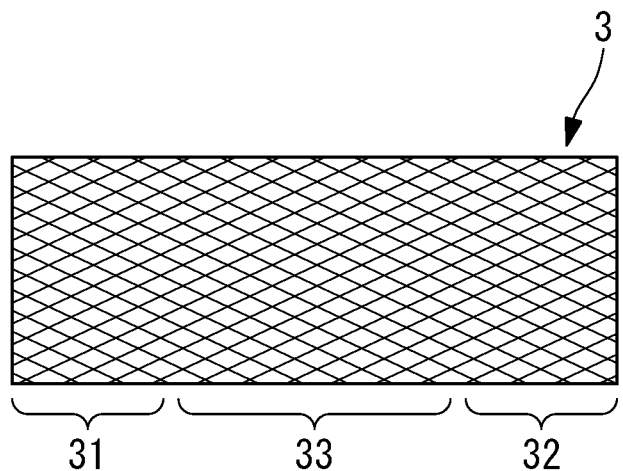
FIG. 2A is a diagram showing a non-expanded state of a stent in the stent delivery system in FIG. 1.
Figure 2B:
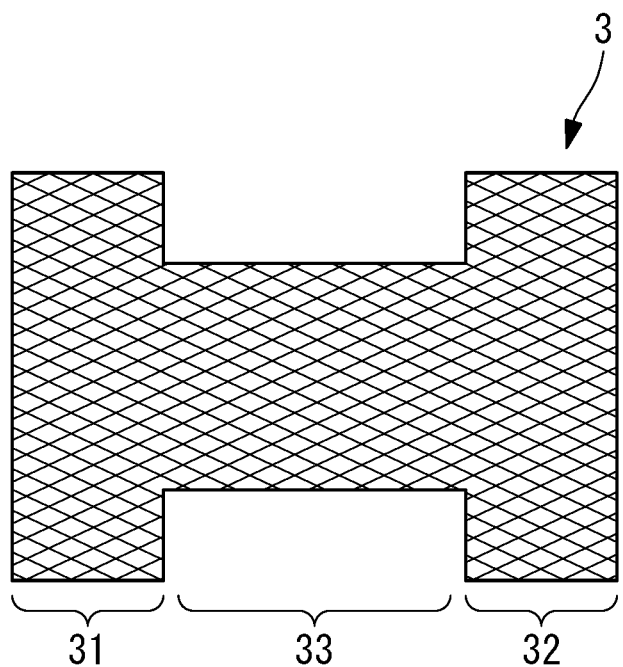
FIG. 2B is a diagram showing an expanded state of the stent in the stent delivery system in FIG. 1.

The stent 3 is a self-expanding stent. As shown in FIGS. 2A and 2B, the stent 3 includes a first expandable part 31, a second expandable part 32, and a waist area 33 between the first expandable part 31 and the second expandable part 32. The first expandable part 31 is an area including the base end of the stent 3. The second expandable part 32 is an area including the distal end of the stent 3. The first expandable part 31 and the second expandable part 32 are disposed a certain distance from each other in the longitudinal direction of the stent 3 (i.e., the direction parallel to the central axis). The stent 3 is attached to the outer circumference of the distal end portion of the inner tube 2 so as to be coaxial with the inner tube 2. The second expandable part 32 is disposed on the side closer to the distal end than the first expandable part 31 is.

The first and second expandable parts 31 and 32 are capable of self-expanding in the radial direction, which is perpendicular to the central axis, from a non-expanded state (compressed state) to an expanded state. As shown in FIG. 2A, in the stent 3, the first and second expandable parts 31 and 32 in the non-expanded state have substantially the same outside diameter as the outside diameter of the waist area 33. In this case, in the expanded state, the stent 3 has a substantially constant outside diameter over the overall length in the longitudinal direction. Preferably, as shown in FIG. 2B, in the stent 3, the first and second expandable parts 31 and 32 in the expanded state may have a larger outside diameter than the waist area 33 and the first and second expandable parts 31 and 32 in the non-expanded state. In other words, in this case, in the non-expanded state, the compression ratio of the expandable parts 31 and 32 in the radial direction is greater than that of the waist area 33.

The outer sheath 4 is a long, circular-tube-like member having flexibility. A handle 7, via which the operator operates the outer sheath 4, is joined to the base end of the outer sheath 4. The inside diameter of the outer sheath 4 is larger than the outside diameter of the inner tube 2. The inner tube 2 is disposed inside the outer sheath 4 so as to extend along the outer sheath 4 in the longitudinal direction. The inner tube 2 and the outer sheath 4 can move relative to each other in the longitudinal direction. The distal end of the outer sheath 4 is disposed at a position away from the distal end of the inner tube 2 toward the base-end side.

The cover 5 is a short cylindrical member having an inside diameter that is larger than the outside diameter of the inner tube 2. The inner tube 2 is disposed inside the cover 5 so as to extend in the longitudinal direction. The cover 5 is disposed between the distal end of the outer sheath 4 and the distal end of the inner tube 2, and the distal end of the cover 5 is joined to the distal end of the inner tube 2.

A cylindrical space for accommodating the stent 3 with the first and second expandable parts 31 and 32 in the non-expanded state is formed between the inner circumferential surfaces of the distal end portion of the outer sheath 4 and the cover 5 and the outer circumferential surface of the distal end portion of the inner tube 2. The first expandable part 31 is disposed between the outer circumferential surface of the inner tube 2 and the inner circumferential surface of the outer sheath 4 and is maintained in the non-expanded state due to the rigidity of the outer sheath 4. The second expandable part 32 is disposed between the outer circumferential surface of the inner tube 2 and the inner circumferential surface of the cover 5 and is maintained in the non-expanded state due to the rigidity of the cover 5. The inner tube 2, the outer sheath 4, and the cover 5 are movable in the longitudinal direction relative to the stent 3.

The cover 5 is configured to be pulled inside the stent 3 while being deformed to a shape having an outside diameter that is smaller than the inside diameter of the stent 3 due to the movement of the inner tube 2 toward the base-end side relative to the stent 3. Such a cover 5 may be formed by folding back the distal-end side area of the flexible inner tube 2 to the outside.

The outer sheath 4 and the cover 5 have walls 10a and 10b for restricting the position of the stent 3 relative to the inner tube 2, the outer sheath 4, and the cover 5 in the longitudinal direction. The wall 10a projects radially inward from the inner circumferential surface of the outer sheath 4, and the wall 10b projects radially inward from the inner circumferential surface of the cover 5. In a state in which the distal-end face of the outer sheath 4 and the base-end face of the cover 5 abut on each other, the base-end face of the stent 3 abuts on the wall 10a, and the distal-end face of the stent 3 abuts on the wall 10b.

Preferably, a stopper 8 for fixing the relative positions of the inner tube 2 and the outer sheath 4 is provided. A hole 9a extending in the radial direction is provided in the side wall of the inner tube 2, and a hole 9b extending in the radial direction is provided in the handle 7 on the outer sheath 4. The hole 9b is open in the outer circumferential surface of the handle 7. The hole 9b may be provided in the side wall of the outer sheath 4, instead of the handle 7. The stopper 8 is a member inserted into the holes 9a and 9b, and examples thereof include a pin, a screw, a rod, and a plate. As a result of the stopper 8 being inserted into the holes 9a and 9b communicating with each other in the radial direction of the inner tube 2 and the outer sheath 4, the inner tube 2 and the outer sheath 4 are fixed at predetermined relative positions at which the distal-end face of the outer sheath 4 abuts on the base-end face of the cover 5.

Next, a stent delivery method using the stent delivery system 1 will be described below, taking pancreatic cyst drainage as an example.

As shown in FIG. 3, the stent delivery method according to this embodiment includes: step S1 in which the stent 3 is inserted into the stomach (alimentary canal) S while the first and second expandable parts 31 and 32 are in the non-expanded state; step S2 in which through-holes Hs and Hc are formed in a stomach wall Ws and a pancreatic cyst wall Wc so as to communicate with each other; step S3 in which the stent 3 is inserted through the through-holes Hs and Hc from the stomach S side to dispose the first expandable part 31 in the stomach S and the second expandable part 32 in the pancreatic cyst C; step S4 in which the first expandable part 31 is expanded in the stomach S; step S5 in which the second expandable part 32 is expanded in the pancreatic cyst C after step S4; and step S6 in which the cover 5 and the inner tube 2 are removed from inside the pancreatic cyst C into the stomach S.

Figure 4A:
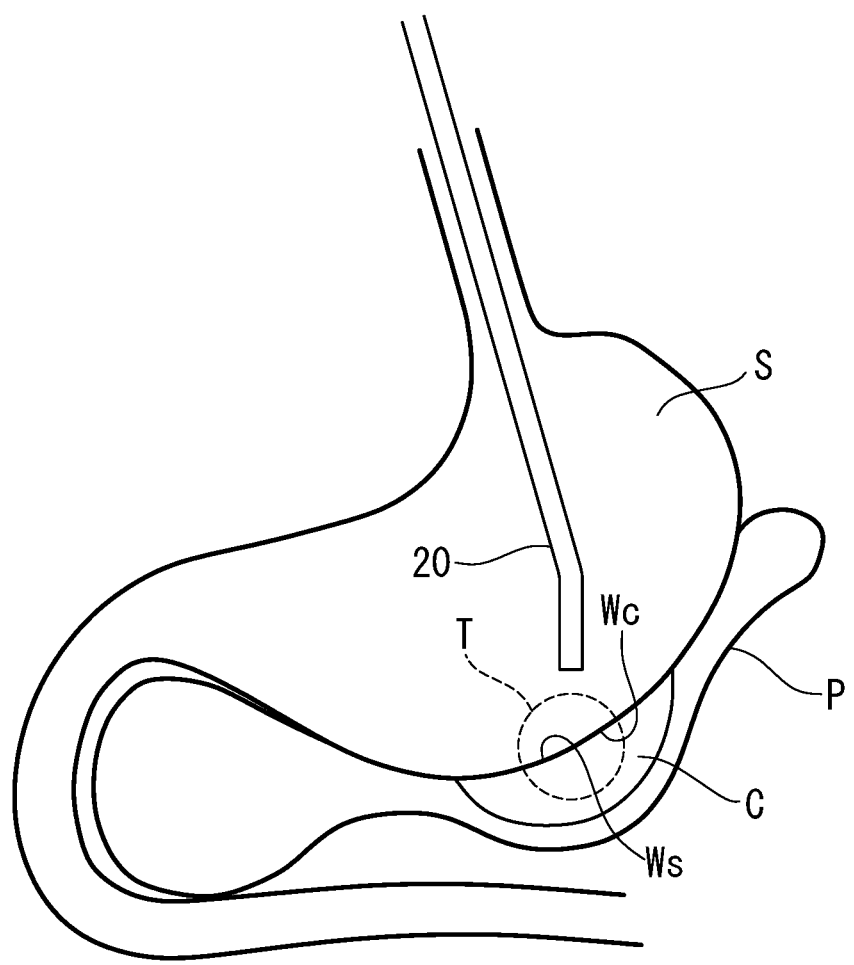
FIG. 4A is a diagram for explaining the stent delivery method according to the embodiment of the present invention.

In step S1, as shown in FIG. 4A, an optical endoscope 20 is inserted into the stomach S from the mouth of the patient, and the distal end of the endoscope 20 is placed near a treatment target site T, at which the stomach wall Ws and the pancreatic cyst wall Wc adjoin each other. Reference sign P in FIG. 4A is the pancreas. Next, the stent delivery system 1 is inserted into the stomach S through a treatment tool channel in the endoscope 20, and the distal end portion of the stent delivery system 1 is placed near the treatment target site T. The stomach wall Ws and the distal end portion of the stent delivery system 1 projecting from the treatment tool channel can be optically observed through the endoscope 20.

Next, in step S2, as shown in FIG. 4B, by using a puncture needle (not shown), through-holes Hs and Hc communicating with each other are formed in the stomach wall Ws and the pancreatic cyst wall Wc at the treatment target site T. The puncture needle may be inserted into the stomach S via, for example, the inside of the inner tube 2.

Alternatively, for example, the puncture needle may be attached to the distal end of the stent delivery system 1. Furthermore, step S2 may be performed before step S1. For example, it is possible that the puncture needle is removed after the through-holes Hs and Hc are formed with the puncture needle, and then the stent delivery system 1 is inserted into the alimentary canal to place the stent 3.

Next, in step S3, as shown in FIG. 4B, the waist area 33 is made to pass through the through-holes Hs and Hc, and the stent 3 is placed so as to straddle the pancreatic cyst C and the stomach S. As a result, the first expandable part 31 is placed in the stomach S, and the second expandable part 32 is placed in the pancreatic cyst C.

Next, in step S4, the first expandable part 31 in the stomach S is expanded in the radial direction from the non-expanded state to the expanded state.

Figure 4C:
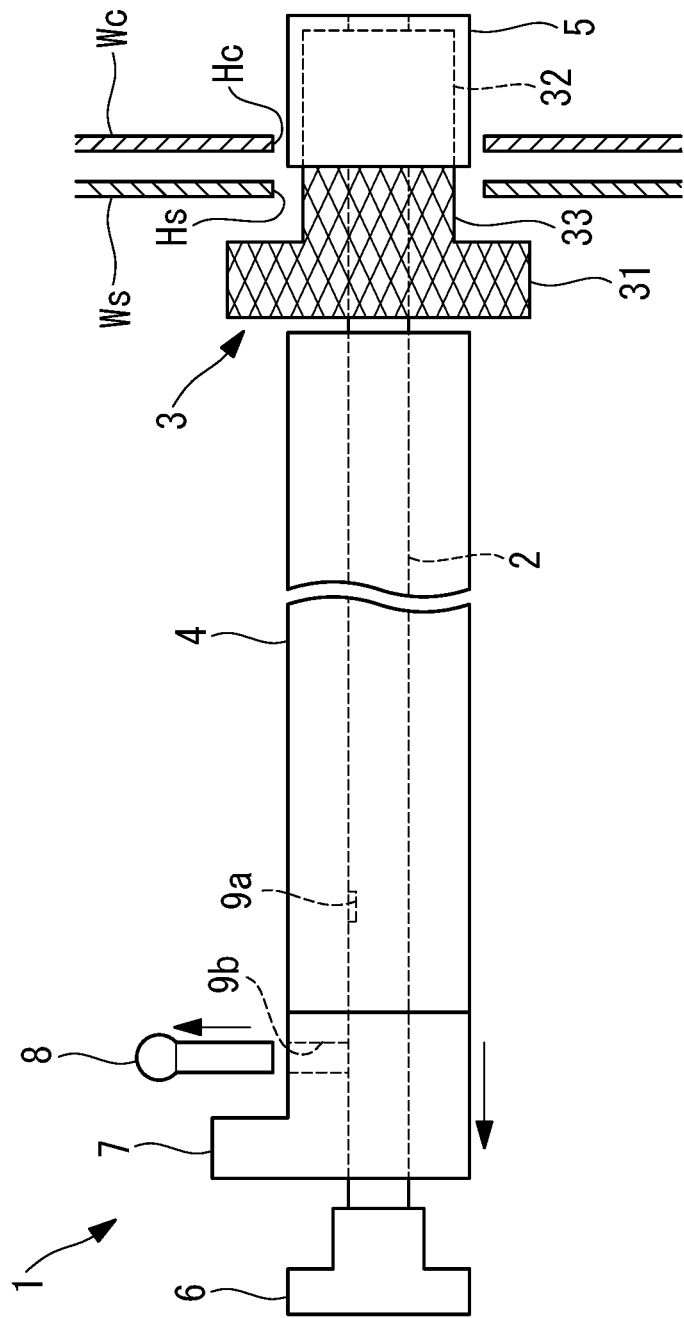
FIG. 4C is a diagram for explaining the stent delivery method according to the embodiment of the present invention.

More specifically, as shown in FIG. 4C, the stopper 8 is removed from the holes 9a and 9b, unfixing the inner tube 2 and the outer sheath 4. Next, by pulling the handle 7 while maintaining the position of the handle 6, the outer sheath 4 is moved toward the base-end side (that is, toward the side opposite from the second expandable part 32), relative to the inner tube 2 and the stent 3. As a result, the first expandable part 31 is exposed in the stomach S, self-expanding from the non-expanded state to the expanded state. In other words, as a result of the constraint (radially inward compression) on the first expandable part 31 by the outer sheath 4 being removed, and the first expandable part 31 transits from the non-expanded state to the expanded state in the stomach S.

Next, in step S5, the second expandable part 32 in the pancreatic cyst C is expanded in the radial direction from the non-expanded state to the expanded state.

Figure 4E:
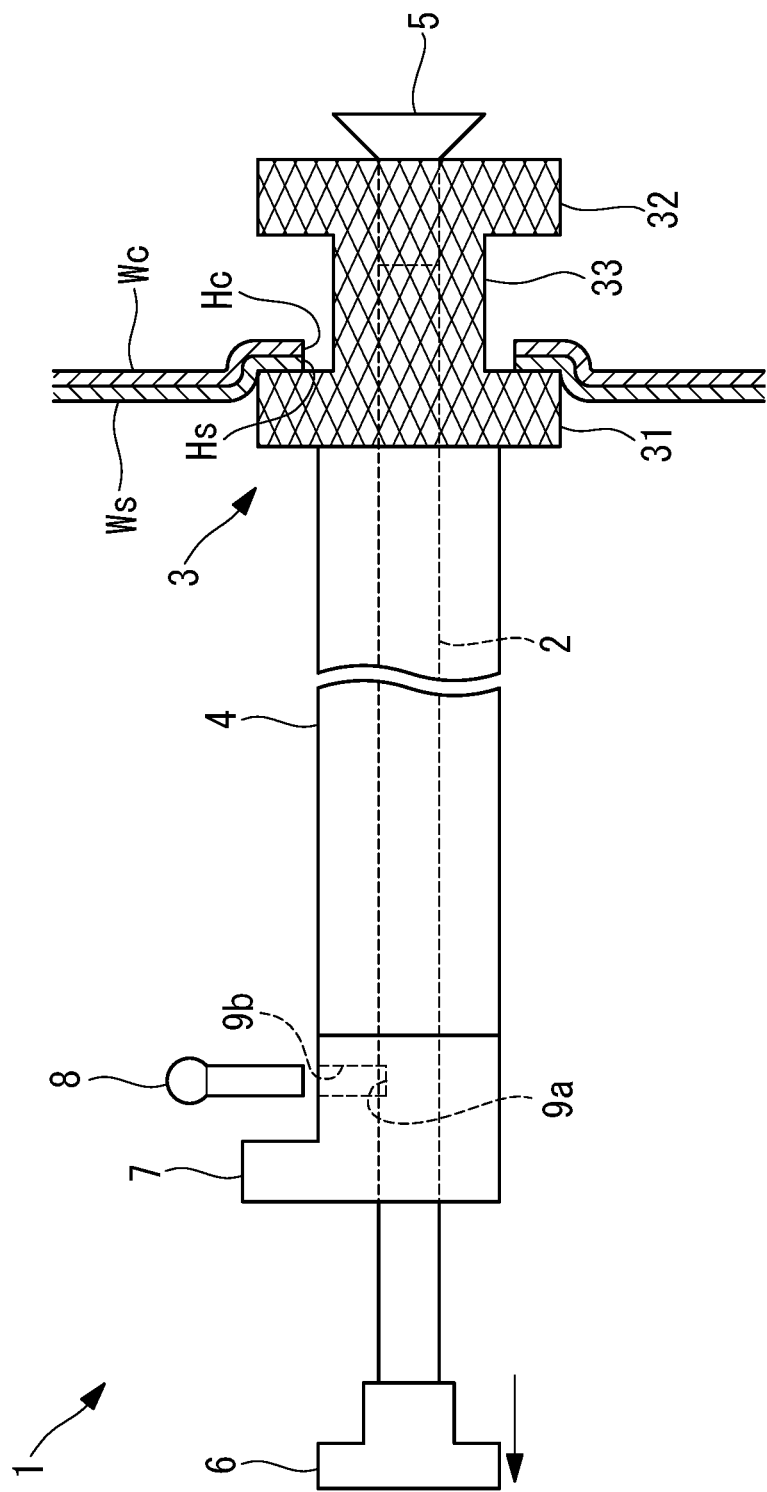
FIG. 4E is a diagram for explaining the stent delivery method according to the embodiment of the present invention.

More specifically, as shown in FIG. 4E, by pulling the handle 6, the inner tube 2 is moved toward the base-end side relative to the stent 3. As a result, the cover 5 moves toward the distal-end side (that is, toward the side opposite from the first expandable part 31) relative to the stent 3, and the second expandable part 32 is exposed in the pancreatic cyst C, self-expanding from the non-expanded state to the expanded state. In other words, as shown in FIG. 4E, in a state in which the base-end part of the cover 5 covering the second expandable part 32 (in the non-expanded state) is located in front of the distal end of the stent 3, the constraint (radially inward compression) on the second expandable part 32 by the cover 5 is removed, and the second expandable part 32 transits from the non-expanded state to the expanded state in the pancreatic cyst C.

The first and second expandable parts 31 and 32, which have larger diameters than the through-holes Hs and Hc, are engaged with the stomach wall Ws and the pancreatic cyst wall Wc, respectively, thus preventing the movement of the stent 3 in the longitudinal direction relative to the walls Ws and Wc.

Herein, in step S5, as shown in FIG. 4D, by moving the handle 7 toward the distal-end side, the first expandable part 31 in the expanded state is pressed against the stomach wall Ws with the distal end of the outer sheath 4, and the stomach wall Ws is pressed toward the pancreatic cyst C from inside the stomach S with the first expandable part 31 in the expanded state. By pressing the stomach wall Ws, the stomach wall Ws is brought into tight contact with the pancreatic cyst wall Wc. Then, as shown in FIG. 4E, the second expandable part 32 is expanded in the pancreatic cyst C while the stomach wall Ws is pressed toward the pancreatic cyst C from inside the stomach S. As a result, it is possible to indwell the stent 3 in a state in which the stomach wall Ws and the pancreatic cyst wall Wc are in tight contact with each other, and moreover, it is possible to reliably hold the stomach wall Ws and the pancreatic cyst wall Wc between the first and second expandable parts 31 and 32 in the expanded state.

Figure 4F:
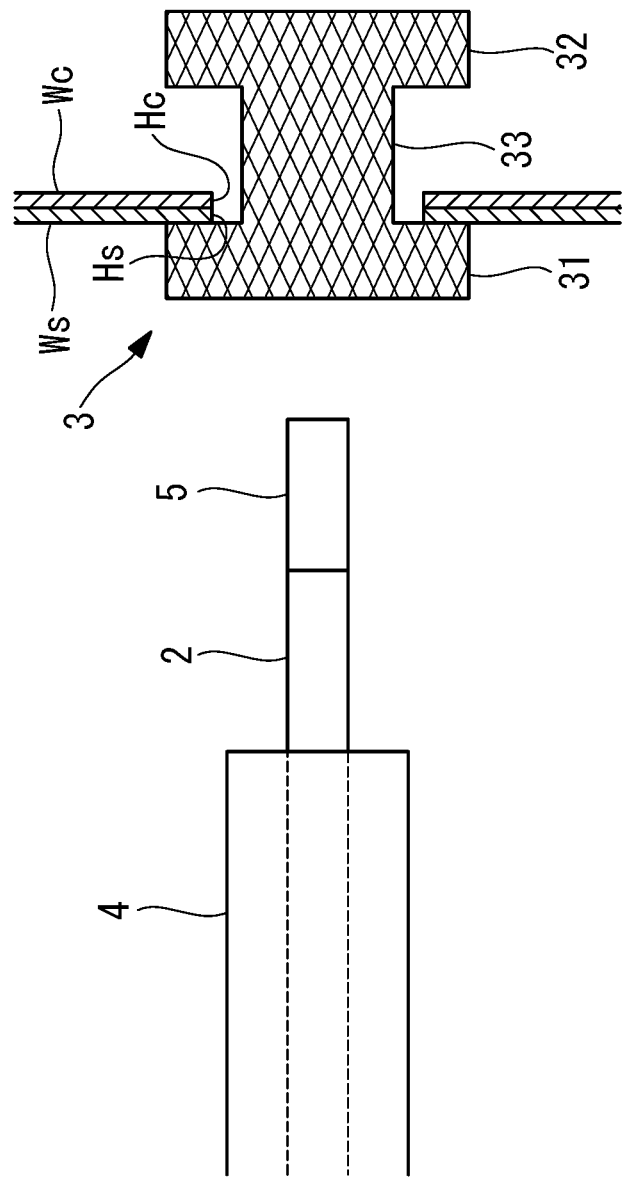
FIG. 4F is a diagram for explaining the stent delivery method according to the embodiment of the present invention.

Next, in step S6, by pulling the handle 6, the entire cover 5 is accommodated in the stent 3. Next, by pulling the handle 6 and the handle 7, as shown in FIG. 4F, the cover 5 and the inner tube 2 are removed from inside the pancreatic cyst C into the stomach S and are separated from the stent 3. As a result, indwelling of the stent 3 through the walls Ws and Wc is completed.

The inside of the pancreatic cyst C and the inside of the stomach S communicate with each other through the interior of the stent 3. Hence, it is possible to discharge the body fluid inside the pancreatic cyst C into the stomach S through the interior of the stent 3.

If the second expandable part 32 inside the pancreatic cyst C is expanded before the first expandable part 31 inside the stomach S is expanded, the second expandable part 32 in the expanded state needs to be pulled toward the stomach S side to bring the pancreatic cyst wall Wc and the stomach wall Ws into tight contact with each other. In this case, it is impossible to observe the second expandable part 32 inside the pancreatic cyst C with the optical endoscope 20 inside the stomach S. Although it is possible to observe the second expandable part 32 inside the pancreatic cyst C with an ultrasonic endoscope inside the stomach S, because ultrasonic endoscope images are less clear than optical endoscope images, it is difficult to accurately know the shape of the second expandable part 32 from the ultrasonic endoscope images. Hence, the second expandable part 32 in the expanded state can be deformed by a too strong pull, or the second expandable part 32 can slip from the pancreatic cyst C into the stomach S via the through-holes Hs and Hc.

In this embodiment, the first expandable part 31 inside the stomach S is expanded, and then the second expandable part 32 inside the pancreatic cyst C is expanded. Hence, through the optical endoscope 20 inside the stomach S, the operator can clearly observe the first expandable part 31 in the expanded state pressing the stomach wall Ws. This configuration provides an advantage in that the operator can press, with the first expandable part 31, the stomach wall Ws toward the pancreatic cyst C from inside the stomach S, while confirming that the shape and position of the first expandable part 31 in the expanded state are properly maintained.

Figure 5A:
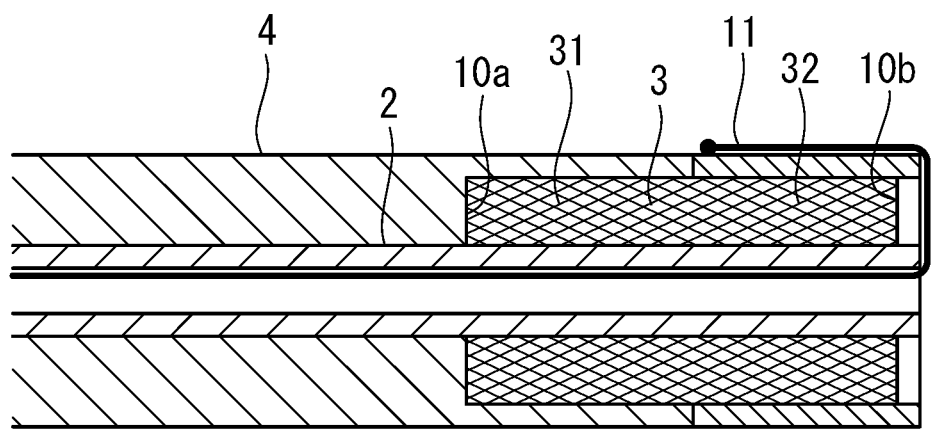
FIG. 5A is a vertical sectional view of a modification of the stent delivery system in FIG. 1.
Figure 5B:
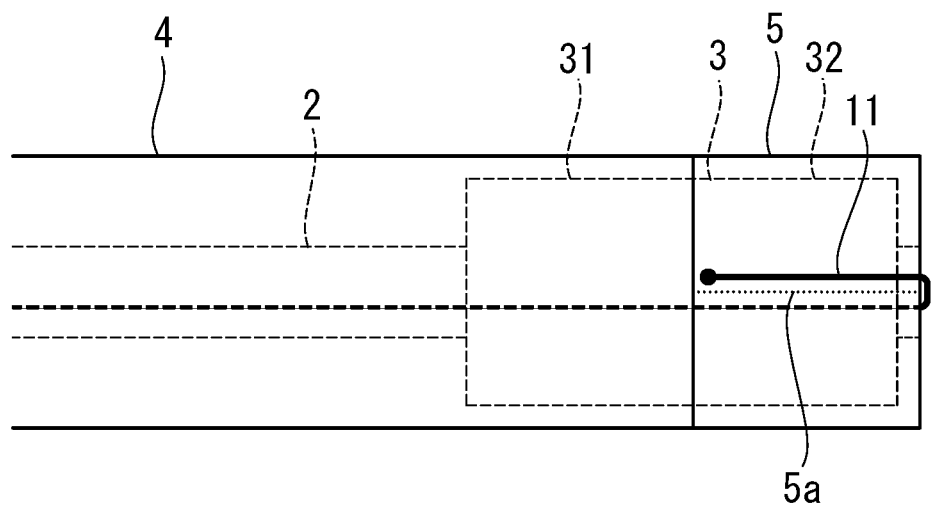
FIG. 5B is a side view of the stent delivery system in FIG. 5A, as viewed from the upper side in FIG. 5A.

In this embodiment, although the cover 5 is moved toward the distal-end side by pulling the inner tube 2, instead, as shown in FIGS. 5A and 5B, a member 11 for flipping the cover 5 may be provided.

The member 11 is a long, fine-diameter member, such as thread. The member 11 passes through the inner tube 2, and the distal end of the member 11 is joined to the base-end part of the cover 5. By pulling the base end of the member 11, it is possible to flip the cover 5 and expose the second expandable part 32.

As shown in FIG. 5B, a perforation line 5a extending in the longitudinal direction may be provided in the cover 5. By pulling the member 11, the cover 5 is torn along the perforation line 5a, and thus it is possible to more easily flip the cover 5.

Figure 6A:
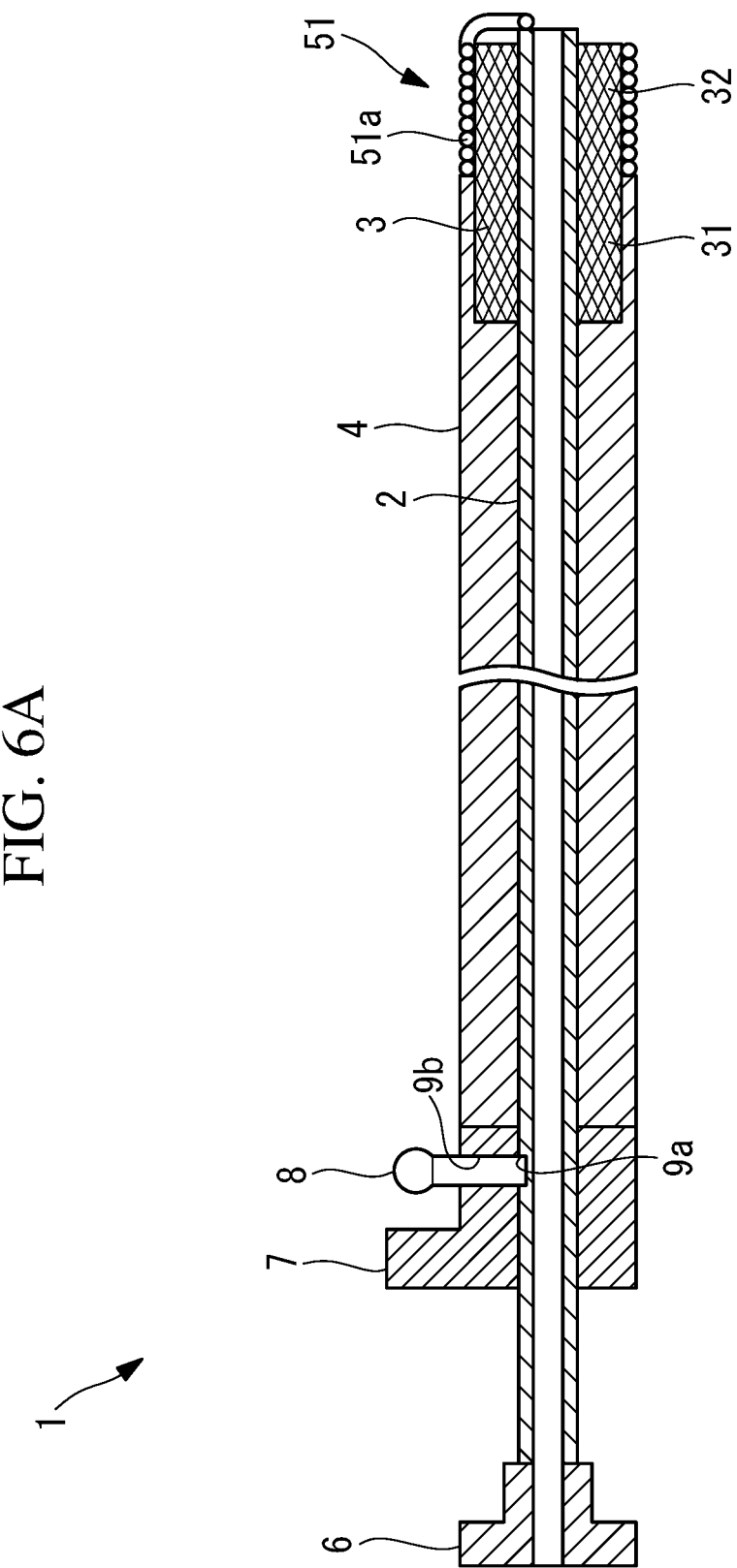
FIG. 6A is a vertical sectional view of another modification of the stent delivery system in FIG. 1.

In this embodiment, the cover 5 has been described as a tubular member that can be deformed by pulling the inner tube 2. Instead, as shown in FIG. 6A, a cover 51 may be formed of a thread 51a that is wound around the second expandable part 32 of the stent 3.

One end of the thread 51a is a fixed end, which is fixed to the distal end of the inner tube 2. The other end of the thread 51a is a free end and is wound around the second expandable part 32. In step S5, as a result of the inner tube 2 being moved toward the distal-end side relative to the stent 3, the fixed end of the thread 51a is pulled toward the side opposite from the first expandable part 31 (i.e., the distal-end side of the first expandable part 31), unwinding the thread 51a and, as a result, causing the second expandable part 32 to self-expand. In other words, in a state in which the thread 51a wound around the outer circumference of the second expandable part 32 is unwound, the constraint (radially inward compression) on the second expandable part 32 by the thread 51a is removed, and the second expandable part 32 transits from the non-expanded state to the expanded state inside the pancreatic cyst C.

Figure 6B:
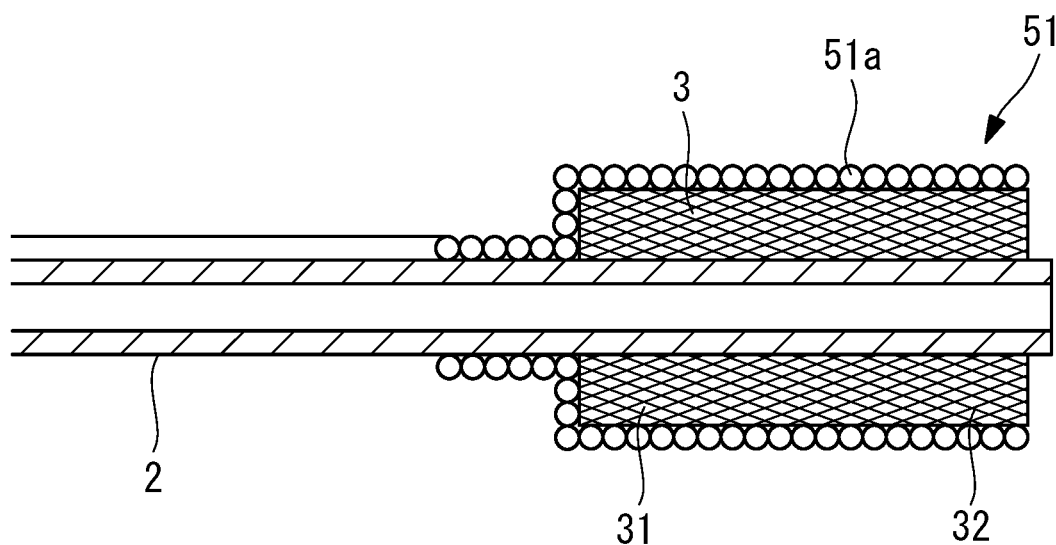
FIG. 6B is a vertical sectional view of another modification of the stent delivery system in FIG. 1.

As shown in FIG. 6B, the thread 51a may be wound from the distal end to the base end of the stent 3. In this case, the distal end (first end) of the thread 51a is located at the distal-end side of the stent 3. The thread 51a extends along the inner tube 2 up to the handle 6, and the base end (second end) of the thread 51a is located at the handle 6 (base-end side of the inner tube 2). When the base end of the thread 51a is pulled, the thread 51a wound around the stent 3 is unwound sequentially from the base-end side, allowing the first expandable part 31 to expand. If the thread 51a continues to be pulled, the thread 51a wound around the second expandable part 32 is unwound, allowing the second expandable part 32 to expand. In other words, by pulling the second end of the thread 51a, the constraint on the first expandable part 31 by the thread 51a is removed, allowing the first expandable part 31 to expand. After the first expandable part 31 has expanded, the constraint (radially inward compression) on the second expandable part 32 by the thread 51a is removed, allowing the second expandable part 32 to expand. Hence, similarly to the case where the cover 5 and the outer sheath 4 are used, it is possible to allow the first expandable part 31 to expand first and the second expandable part 32 to expand next. With this configuration, it is possible to reduce the diameter of the distal end portion of the stent delivery system 1, compared with a case where the outer sheath 4 is used. Furthermore, because the thread 51a does not pass through the lumen of the inner tube 2, it is possible to reduce the resistance occurring when the thread 51a is pulled. In a modification in FIG. 6B, the stent 3 whose outside diameter in the expanded state is substantially constant over the overall length in the longitudinal direction is used.

In this embodiment, to enable the cover 5 to be removed from inside the pancreatic cyst C, the cover 5 is configured to be deformable until the diameter thereof is smaller than the inside diameter of the stent 3. However, instead, the inside diameter of the stent 3 may be increased until it is larger than the outside diameter of the cover 5.

Figure 7A:
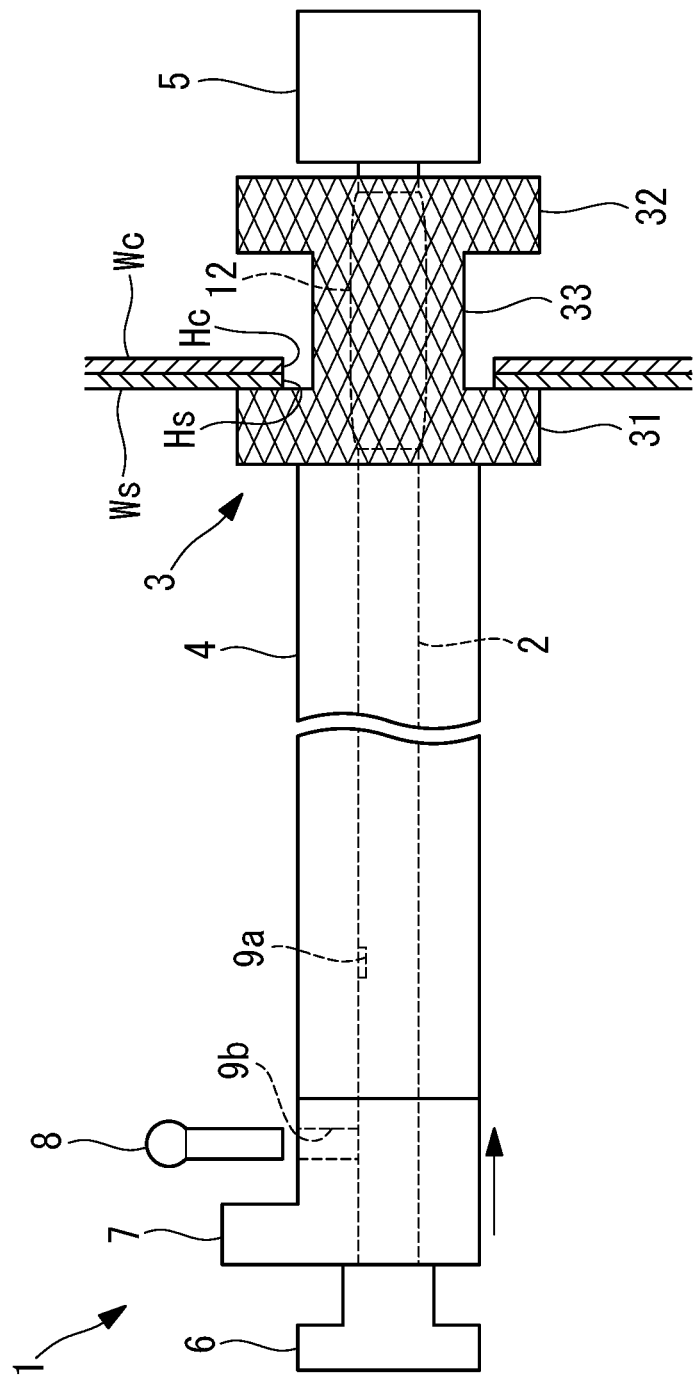
FIG. 7A is a diagram for explaining a modification of a method for removing a cover from inside a pancreatic cyst.

In this case, as shown in FIG. 7A, in step S5, by pressing the handle 6, the inner tube 2 and the cover 5 are moved toward the distal-end side relative to the stent 3, allowing the second expandable part 32 to be exposed and self-expand.

Figure 7B:
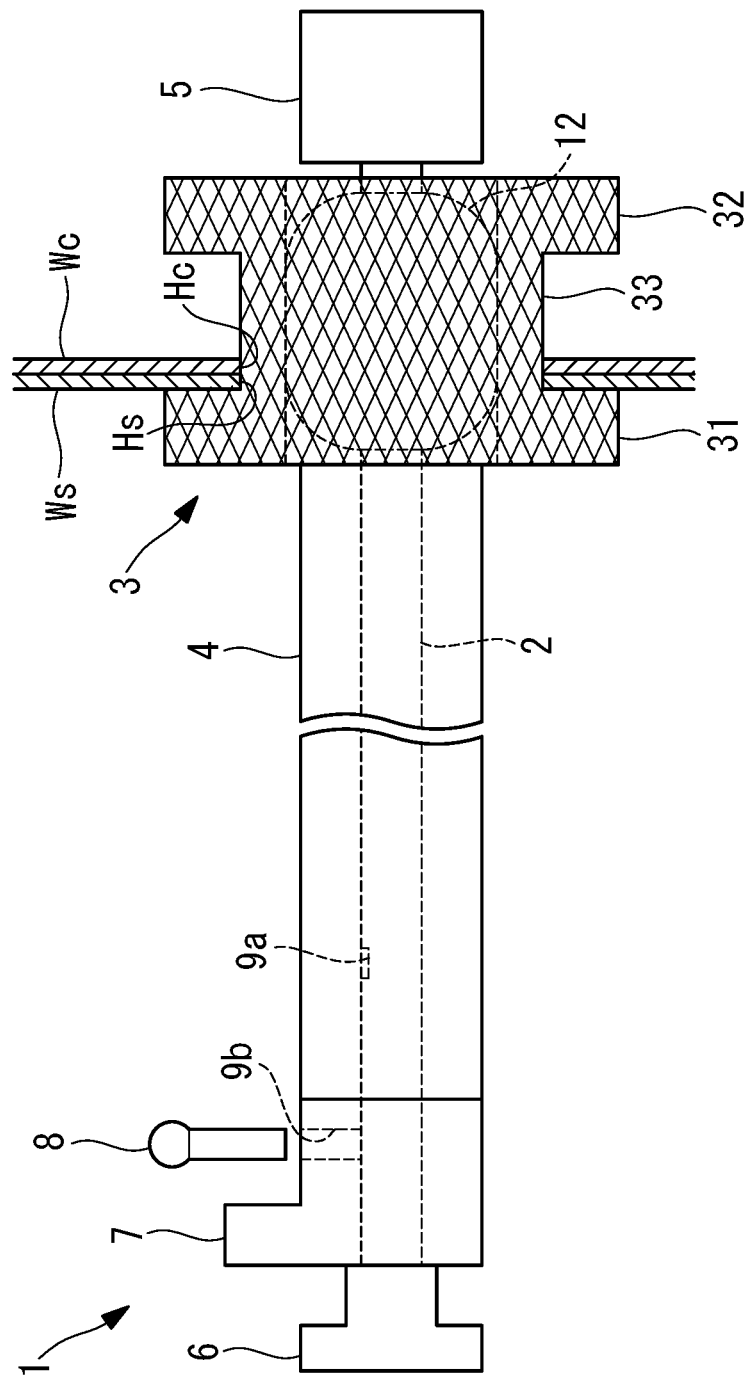
FIG. 7B is a diagram for explaining a modification of a method for removing a cover from inside a pancreatic cyst.
Figure 7C:
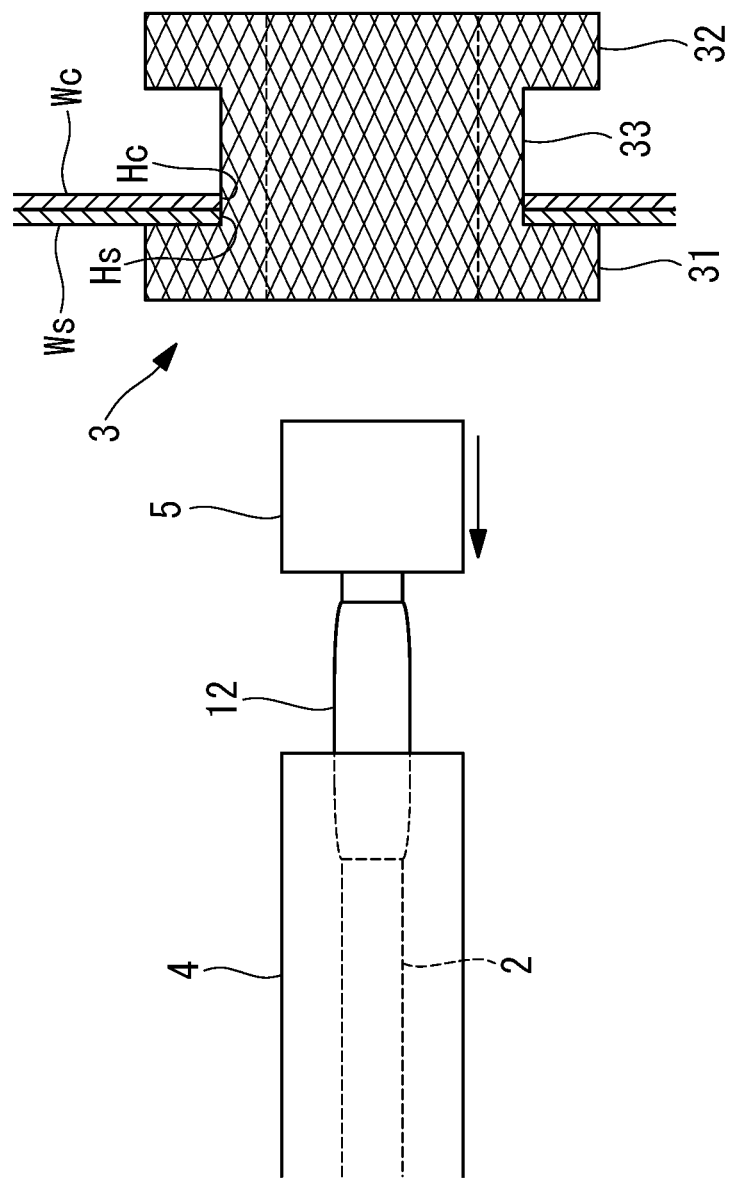
FIG. 7C is a diagram for explaining a modification of a method for removing a cover from inside a pancreatic cyst.

Next, as shown in FIG. 7B, for example, the entire stent 3 is expanded by a balloon 12, and the inside diameter of the entire stent 3 exceeds the outside diameter of the cover 5. Next, as shown in FIG. 7C, by pulling the handle 6 and the handle 7, the cover 5 and the inner tube 2 are removed from inside the pancreatic cyst C into the stomach S through the interior of the stent 3.

The stent 3 may be self-expanded. Alternatively, as shown in FIGS. 7A to 7C, a mechanism for expanding the stent 3, such as, for example, the balloon 12, may be provided between the inner tube 2 and the stent 3.

Although a case where the stent 3 is used for the stomach and the pancreatic cyst has been described in this embodiment, the site to which the stent delivery method according to this embodiment is used is not limited to these sites, and the stent delivery method according to this embodiment may be applied to other alimentary canals and cysts. For example, the stent 3 may be used in the stomach and the common bile duct, or the stomach and the intrahepatic bile duct.

From the embodiment above, the following aspects of the invention are derived.

An aspect of the present invention is a stent delivery method using a tubular stent having a first expandable part and a second expandable part, the first and second expandable parts being provided at positions away from each other in a direction parallel to the central axis of the stent, the first and second expandable parts being expandable from a non-expanded state to an expanded state, in which the outside diameters of the first and second expandable parts are larger than those in the non-expanded state. The method includes: forming through-holes in an alimentary canal wall and a cyst wall so as to communicate with each other, the cyst being formed outside the alimentary canal, and the cyst wall adjoining the alimentary canal wall; inserting the stent through the through-holes and placing the first expandable part in the alimentary canal and the second expandable part in the cyst; allowing the first expandable part to expand to the expanded state in the alimentary canal; and after the expansion of the first expandable part, allowing the second expandable part to expand in the cyst while pressing the wall of the alimentary canal with the first expandable part in the expanded state.

According to this aspect, the stent whose first and second expandable parts are in the non-expanded state is placed so as to pass through the through-holes formed in the walls of the alimentary canal and the cyst. Then, the first expandable part in the alimentary canal and the second expandable part in the cyst are expanded from the non-expanded state to the expanded state. The first and second expandable parts in the expanded state inhibit movement of the stent in a direction parallel to the central axis thereof relative to the walls of the alimentary canal and the cyst.

In this case, the first expandable part is expanded before the second expandable part is expanded. Hence, it is possible to properly operate the stent while the position and shape of the first expandable part in the expanded state are observed with an endoscope inserted into the alimentary canal.

Furthermore, by pressing the alimentary canal wall with the first expandable part in the expanded state, the alimentary canal wall is brought into tight contact with the cyst wall. Hence, by allowing the second expandable part to expand in a state in which the alimentary canal wall is in tight contact with the cyst wall, it is possible to reliably hold the alimentary canal and the cyst wall between the first and second expandable parts in the expanded state.

In the above aspect, the alimentary canal may be the stomach, and the cyst may be the pancreatic cyst.

In the above aspect, the stent delivery method may further include, before forming the through-holes, inserting the stent into the alimentary canal with the first and second expandable parts being in the non-expanded state.

In the above aspect, the stent may be attached to the outer circumference of a distal end portion of an inner tube. In a state in which the stent is attached to the outer circumference of the distal end portion of the inner tube, the second expandable part may be located closer to the distal-end side than the first expandable part is. An outer sheath and a cover may respectively cover the outer circumference of the first expandable part and the outer circumference of the second expandable part in the non-expanded state, the outer sheath and the cover being movable in a direction parallel to the central axis of the stent, relative to the stent. The allowing the first expandable part to expand may include moving the outer sheath toward the base-end side, relative to the stent, to remove radially inward compression of the first expandable part by the outer sheath. The allowing the second expandable part to expand may include moving the cover toward the distal-end side, relative to the stent, to remove radially inward compression of the second expandable part by the cover.

With this configuration, it is possible to control the expansion of the first expandable part from the non-expanded state to the expanded state by operating the outer sheath and to control the expansion of the second expandable part from the non-expanded state to the expanded state by operating the cover.

In the above aspect, the cover may be formed of a thread wound around the circumference of the second expandable part of the stent, a portion of the thread being joined to the inner tube. The allowing the second expandable part to expand may include moving the inner tube toward the distal-end side, relative to the stent, thus pulling the thread and allowing the thread wound around the circumference of the second expandable part to be unwound.

With this configuration, it is possible to control the expansion of the second expandable part from the non-expanded state to the expanded state by operating the inner tube. Furthermore, it is possible to easily remove the unwound thread from inside the cyst into the alimentary canal through the interior of the stent.

In the above aspect, the stent delivery method may further include, after the expansion of the second expandable part, allowing the inside diameter of the stent to increase to a diameter larger than the outside diameter of the cover.

With this configuration, it is possible to remove the cover from inside the cyst into the alimentary canal through the interior of the expanded stent. Furthermore, because it is possible to remove the cover from inside the cyst without deforming the cover, the design flexibility of the cover is improved.

In the above aspect, the stent may be attached to the outer circumference of a distal end portion of an inner tube. In a state in which the stent is attached to the outer circumference of the distal end portion of the inner tube, the second expandable part may be located closer to the distal-end side than the first expandable part is. A thread may be wound around the outer circumferences of the first and second expandable parts in the non-expanded state, a first end of the thread being located at the distal-end side of the stent, a second end of the thread being located at the base-end side of the inner tube. The allowing the first expandable part to expand may include pulling the second end of the thread to remove radially inward compression of the first expandable part by the thread. The allowing the second expandable part to expand may include, after the expansion of the first expandable part, additionally pulling the second end of the thread to remove the radially inward compression of the second expandable part by the thread.

With this configuration, it is possible to allow the first expandable part and the second expandable part to sequentially expand by a simple operation in which simply the second end of the thread is kept pulled.

REFERENCE SIGNS LIST 1 stent delivery system
2 inner tube
3 stent
31 first expandable part
32 second expandable part
33 waist area
4 outer sheath
5 cover
6, 7 handle
8 stopper
9a, 9b hole
10a, 10b wall
11 member
20 optical endoscope
S stomach (alimentary canal)
C pancreatic cyst (cyst)
Hs, Hc through-hole
Ws stomach wall
We pancreatic cyst wall

The invention claimed is:

1. A stent delivery method using a tubular stent having a first expandable part and a second expandable part, the first and second expandable parts being provided at positions away from each other in a direction parallel to a central axis of the stent, the first and second expandable parts being expandable from a non-expanded state to an expanded state, in which the outside diameters of the first and second expandable parts are larger than those in the non-expanded state, the method comprising:

inserting an endoscope into an alimentary canal;
forming a first though-hole in a wall of the alimentary canal and forming a second through-hole in a wall of a cyst such that the alimentary canal and the cyst communicate with each other through the first and second through-holes, the cyst being formed outside the alimentary canal, and the wall of the cyst adjoining the wall of the alimentary canal;
inserting the stent through the first and second through-holes such that the first expandable part is placed in the alimentary canal and the second expandable part is placed in the cyst;
allowing the first expandable part to expand to the expanded state in the alimentary canal; and
while observing, by the endoscope, the first expandable part in the expanded state, allowing the second expandable part to expand in the cyst while moving the first expandable part distally to press the wall of the alimentary canal with the first expandable part in the expanded state.

2. The stent delivery method according to claim 1, wherein the alimentary canal is the stomach, and the cyst is the pancreatic cyst.

3. The stent delivery method according to claim 1, further comprising, before forming the first and second through-holes, inserting the stent into the alimentary canal with the first and second expandable parts being in the non-expanded state.

4. The stent delivery method according to claim 1, wherein
the stent is attached to the outer circumference of a distal end portion of an inner tube,
in a state in which the stent is attached to the outer circumference of the distal end portion of the inner tube, the second expandable part is located further distally than the first expandable part,
an outer sheath and a cover respectively cover the outer circumference of the first expandable part and the outer circumference of the second expandable part in the non-expanded state, the outer sheath and the cover being movable in a direction parallel to the central axis of the stent, relative to the stent, the allowing of the first expandable part to expand comprises moving the outer sheath proximally, relative to the stent, to remove a radially inward compression of the first expandable part by the outer sheath, and the allowing of the second expandable part to expand comprises moving the cover distally, relative to the stent, to remove a radially inward compression of the second expandable part by the cover.

5. The stent delivery method according to claim 4, wherein the cover is formed of a thread wound around the circumference of the second expandable part of the stent, a portion of the thread being joined to the inner tube, and the allowing of the second expandable part to expand comprises moving the inner tube distally, relative to the stent, to unwind the thread from around the circumference of the second expandable part.

6. The stent delivery method according to claim 4, further comprising, after the expansion of the second expandable part, allowing the inside diameter of the stent to increase to a diameter larger than the outside diameter of the cover.

7. The stent delivery method according to claim 1, wherein the stent is attached to the outer circumference of a distal end portion of an inner tube, in a state in which the stent is attached to the outer circumference of the distal end portion of the inner tube, the second expandable part is located further distally than the first expandable part, a thread is wound around the outer circumferences of the first and second expandable parts in the non-expanded state, a first end of the thread being located at the distal-end side of the stent, a second end of the thread being located at the base-end side of the inner tube, the allowing of the first expandable part to expand comprises pulling the second end of the thread to remove a radially inward compression of the first expandable part by the thread, and the allowing of the second expandable part to expand comprises, after the expansion of the first expandable part, additionally pulling the second end of the thread to remove the radially inward compression of the second expandable part by the thread.

8. The stent delivery method according to claim 1, wherein the stent is provided in a stent delivery device inserted into a treatment tool channel in the endoscope, the first expandable part is provided further proximally to a base end of the stent delivery device than the second expandable part, and the wall of the alimentary canal is pressed with the first expandable part in the expanded state by pushing the stent delivery device in a direction so as to project from the treatment tool channel.

9. A stent delivery method using a tubular stent having a first expandable part and a second expandable part, the first and second expandable parts being provided at positions away from each other in a direction parallel to a central axis of the stent, the first and second expandable parts being expandable from a non-expanded state to an expanded state, in which the outside diameters of the first and second expandable parts are larger than those in the non-expanded state, the method comprising:

forming through-holes in an alimentary canal wall and a cyst wall so as to communicate with each other, the cyst being formed outside the alimentary canal, and the cyst wall adjoining the alimentary canal wall;

inserting the stent through the through-holes and placing the first expandable part in the alimentary canal and the second expandable part in the cyst;

allowing the first expandable part to expand to the expanded state in the alimentary canal; and after the expansion of the first expandable part, allowing the second expandable part to expand in the cyst while pressing the wall of the alimentary canal with the first expandable part in the expanded state;

wherein the stent is attached to the outer circumference of a distal end portion of an inner tube, in a state in which the stent is attached to the outer circumference of the distal end portion of the inner tube, the second expandable part is located closer to the distal-end side than the first expandable part is, an outer sheath and a cover respectively cover the outer circumference of the first expandable part and the outer circumference of the second expandable part in the non-expanded state, the outer sheath and the cover being movable in a direction parallel to the central axis of the stent, relative to the stent, the allowing the first expandable part to expand includes moving the outer sheath toward the base-end side, relative to the stent, to remove radially inward compression of the first expandable part by the outer sheath, and the allowing the second expandable part to expand includes moving the cover toward the distal-end side, relative to the stent, to remove radially inward compression of the second expandable part by the cover.

10. The stent delivery method according to claim 9, wherein the cover is formed of a thread wound around the circumference of the second expandable part of the stent, a portion of the thread being joined to the inner tube, and the allowing the second expandable part to expand includes moving the inner tube toward the distal-end side, relative to the stent, thus pulling the thread and allowing the thread wound around the circumference of the second expandable part to be unwound.

11. The stent delivery method according to claim 9, further comprising, after the expansion of the second expandable part, allowing the inside diameter of the stent to increase to a diameter larger than the outside diameter of the cover.

12. A stent delivery method using a tubular stent having a first expandable part and a second expandable part, the first and second expandable parts being provided at positions away from each other in a direction parallel to a central axis of the stent, the first and second expandable parts being expandable from a non-expanded state to an expanded state, in which the outside diameters of the first and second expandable parts are larger than those in the non-expanded state, the method comprising:

forming through-holes in an alimentary canal wall and a cyst wall so as to communicate with each other, the cyst being formed outside the alimentary canal, and the cyst wall adjoining the alimentary canal wall;

inserting the stent through the through-holes and placing the first expandable part in the alimentary canal and the second expandable part in the cyst;

allowing the first expandable part to expand to the expanded state in the alimentary canal; and after the expansion of the first expandable part, allowing the second expandable part to expand in the cyst while pressing the wall of the alimentary canal with the first expandable part in the expanded state;
wherein
the stent is attached to the outer circumference of a distal end portion of an inner tube,
in a state in which the stent is attached to the outer circumference of the distal end portion of the inner tube, the second expandable part is located closer to the distal-end side than the first expandable part is,
a thread is wound around the outer circumferences of the first and second expandable parts in the non-expanded state, a first end of the thread being located at the distal-end side of the stent, a second end of the thread being located at the base-end side of the inner tube,
the allowing the first expandable part to expand includes pulling the second end of the thread to remove radially inward compression of the first expandable part by the thread, and
the allowing the second expandable part to expand includes, after the expansion of the first expandable part, additionally pulling the second end of the thread to remove the radially inward compression of the second expandable part by the thread.

* * * * *